(12) United States Patent
Dyer

(10) Patent No.: US 9,918,924 B2
(45) Date of Patent: Mar. 20, 2018

(54) BIPHASIC INJECTABLE COMPOSITIONS FOR TISSUE AUGMENTATION

(71) Applicant: Inna Dyer, Atlanta, GA (US)

(72) Inventor: Wallace K. Dyer, Atlanta, GA (US)

(*) Notice: Subject to any disclaimer, the term of this patent is extended or adjusted under 35 U.S.C. 154(b) by 0 days.

(21) Appl. No.: 14/686,083

(22) Filed: Apr. 14, 2015

(65) Prior Publication Data

US 2016/0058685 A1    Mar. 3, 2016

Related U.S. Application Data

(63) Continuation of application No. 12/830,652, filed on Jul. 6, 2010, now Pat. No. 9,089,594, which is a continuation of application No. 11/738,132, filed on Apr. 20, 2007, now abandoned, which is a continuation of application No. 09/943,138, filed on Aug. 30, 2001, now abandoned.

(60) Provisional application No. 60/229,085, filed on Aug. 30, 2000, provisional application No. 60/229,989, filed on Sep. 5, 2000, provisional application No. 60/241,636, filed on Oct. 19, 2000.

(51) Int. Cl.

| | |
|---|---|
| *A61K 9/16* | (2006.01) |
| *A61K 8/81* | (2006.01) |
| *A61K 9/00* | (2006.01) |
| *A61K 31/74* | (2006.01) |
| *A61L 27/14* | (2006.01) |
| *A61K 8/85* | (2006.01) |
| *A61Q 19/00* | (2006.01) |
| *A61Q 19/08* | (2006.01) |
| *A61K 8/02* | (2006.01) |

(52) U.S. Cl.
CPC .......... *A61K 8/8123* (2013.01); *A61K 8/0241* (2013.01); *A61K 8/8176* (2013.01); *A61K 8/85* (2013.01); *A61K 9/0019* (2013.01); *A61K 9/1635* (2013.01); *A61K 9/1647* (2013.01); *A61K 31/74* (2013.01); *A61L 27/14* (2013.01); *A61Q 19/00* (2013.01); *A61Q 19/08* (2013.01); *A61K 2800/412* (2013.01); *A61K 2800/594* (2013.01); *A61K 2800/91* (2013.01); *A61L 2400/06* (2013.01)

(58) Field of Classification Search
CPC ... A61K 9/1647; A61K 9/1635; A61K 9/1694
See application file for complete search history.

(56) References Cited

U.S. PATENT DOCUMENTS 5,468,401 A * 11/1995 Lum .................... C10M 111/02
508/115

* cited by examiner

*Primary Examiner* — Carlos A Azpuru
(74) *Attorney, Agent, or Firm* — Ballard Spahr LLP

(57) ABSTRACT

Methods and compositions for use in tissue volume replacement are provided. The present invention comprises compositions comprising a combination of materials, comprising preferably a solid polymer particle phase and a gel phase, and also comprises single phase compositions. More particularly, preferred embodiments comprise a solid polymer particle phase made of materials comprising Gore-Tex (micronized e-PTFE), PDS II (polydioxanone, a monofilament), NUROLON (a long chain aliphatic polymer Nylon 6 or Nylon 6,6) ETHILON (a long chain aliphatic polymer Nylon 6 and Nylon 6,6), PROLENE (Polypropylene, isotactic crystalline stereoisomer of polypropylene, a synthetic linear polyolefin.), VICRYL (copolymer made from 90% glycolide and 10% L-lactide), silk, MONACRYL (poly ϵ-caprolactone.), polylactide, polyglycolide, poly lactide-co-glycolide, and BIOPOL (polyhydroxyvalerate), MEDPOR (biocompatible (micronized) polyethylene), BIOGLASS (bioactive glass particulate), NOVABONE and NOVABONE-CM, and the gel phase comprises polyvinylpyrrolidone (PVP). Preferred single phase compositions comprise PVP. Methods of the present invention comprising injection of such compositions for tissue augmentation.

13 Claims, No Drawings

BIPHASIC INJECTABLE COMPOSITIONS FOR TISSUE AUGMENTATION

CROSS-REFERENCE TO RELATED APPLICATIONS

This application claims priority to U.S. Provisional No. 60/229,085 filed Aug. 30, 2000, and to U.S. Provisional Application No. 60/229,989 filed Sep. 5, 2000, and to U.S. Provisional No. 60/241,636 filed Oct. 19, 2000.

TECHNICAL FIELD

This application relates to novel biphasic and single phase compositions for soft tissue volume replacement, and methods of use of such compositions. In addition, the present invention relates to methods for use of such compositions as material in plastic and reconstructive surgery.

BACKGROUND OF THE INVENTION

Plastic and reconstructive surgeons have long sought to develop a safe, predictable, and injectable material for soft tissue volume replacement. Surgeons seek not just to add bulk, but also to restore normal tissue consistency and composition. At present, injectable implant material can be designed to be tolerated by the host and to mimic the tissue it is designed to replace or augment. Even the well-tolerated implant, however, still acts as a foreign body after placement. A layer of host proteins rapidly adsorbs onto the hydrophobic implant surface of most polymers and attempts to degrade the polymer. The denatured proteins elicit an acute inflammatory response from the patient, attracting neutrophils, macrophages, and fibroblasts. Collagen is then deposited over the matrix on the implant, laying the groundwork for subsequent cellular adhesion. The degree of chronic inflammation that persists depends upon the specific qualities of the implant, as well as the local tissue environment.

Implant materials that undergo enzymatic degradation, nonspecific hydrolysis, or stress fragmentation will release breakdown products into the local environment. Local macrophages will generally engulf those particles that are 60 microns or smaller and may transport them to regional lymph nodes. Submicrometer-sized particles are the most easily transported and may remain intracellularly indefinitely. Particles ranging from 20 to 60 microns approach the size of a macrophage and may cause the death of the cell when engulfed. The dead cell then releases its intracellular enzymes, such as cytokines, which then attract more phagocytes. While destroying and engulfing the cellular debris, the phagocytes again encounter the polymer particles, and the cycle continues as a chronic inflammatory response. Many of the following injectable materials have tried to prevent such problems from occurring, but none of the currently available materials have been successful.

Injectable Biologic Material

Bovine collagen and its use as an injectable implant was first developed by Collagen Corporation in 1975 and called ZYDERM™. Bovine collagen is not desirable in facial plastic and reconstructive surgery because most users of ZYPLAST™, another bovine collagen product, describe a clinical effect of merely three to four months, while ZYDERM™'s results were even more short lived.

Mentor Corporation developed another product, FIBREL™, in attempt to simulate the process of wound healing. FIBREL™, which consists of plasma mixed with porcine-derived gelatin and e-aminocaproic acid (e-ACA), is injected intradermally. The plasma serves as a source of fibrin and clotting factors, the gelatin defines the site of the reaction, and the e-ACA limits fibrinolysis. The tissue reaction that occurs upon injection leads to fibrinogen deposition, followed by fibrinolysis and collagen formation. A disadvantage of FIBREL™ is that "touchups" are frequently required. Each of these collagen derivatives, (ZYDERM™, ZYPLAST™, and FIBREL™) are poorly suited for soft tissue augmentation because they rapidly biodegrade, and therefore, their effect is only transitory.

In order to fulfill the need for a natural, nonimmunogenic biologic material that can be produced in mass quantities, both Hylaform/Biomatrix and Q-med Uppsala developed derivatives of hyaluronic acid to be used as injectable soft tissue builders. These products are currently being evaluated by the FDA. Hylaform's HYLAN B™ gel product is an insoluble derivative produced by treating hyaluronic acid with vinyl sulfone. Q-Med Uppsala's RESTYLANE™ product also consists of hyaluronic acid but is cross-linked and processed into a 2% gel. Hyaluronic acid is a polysaccharide that plays an integral role in stabilizing the extracellular matrix, as well as lubricating, hydrating, and increasing its viscoelastic properties. Because hyaluronic acid is not species-specific, it does not elicit a humoral or cell-mediated immune response in the patient. The use of hyaluronic acid as an injectable filler results in greater than 33% improvement at 18 weeks.

Injectable Homologous Material

Collagenesis, Inc. developed the use of DERMALOGEN™, homologous collagen dispersion, which is well tolerated and elicits only a low grade inflammatory response. DERMALOGEN™ is a suspension of processed dermis obtained from AATB-accredited tissue banks. A mechanical process homogenizes the decellularized dermis to produce a suspension of mostly type I collagen, with trace amounts of types III and IV collagen, elastin, fibronectin, chondroitin sulfate, and other proteoglycans.

Similarly, LifeCell Corporation developed a product, ALLODERM™, that is an acellular sheet of meshed dermal proteins prepared from cadaver skin. Surgeons use this material for soft tissue augmentation in a variety of situations. An advantage of this material is that its effect is somewhat long term, lasting greater than one year. A distinct disadvantage is that use of this material requires an incision. Trials of long term efficacy will soon conclude for an injectable form of this material developed by the manufacturer. The injectable form consists of micronized ALLODERM™ particles ranging in size from 60 to 600 microns and is injected into a deep dermal level with a 26 gauge needle.

Injectable Autologous Material

Neuber first reported the use of fat transplantation in 1893, however, lipoaugmentation has several distinct disadvantages. The utility of fat transplantation is questionable because most of the transplanted materials do not survive. Reinjected autologous fat is known to have a resorption rate of approximately 70%, making repeated injections necessary. The ultimate result with fat transplantation depends upon the fibrotic reaction and the necrosis of the reinjected fat.

Isolagen Technologies attempts to enhance production of collagen with its ISOLAGEN™ product, by directly introducing cultured autologous fibroblasts. After a skin biopsy, autologous fibroblasts are isolated and expanded in vitro. A suspension of these fibroblasts is injected into the dermis and has been shown to provide persistent soft tissue augmentation. West and Alster treated eleven patients with ISOLAGEN™ and noted persistent correction in the nasolabial folds six months after the injection. In addition, Watson et al. found that injected fibroblasts seemed to be incorporated into the dermis and lead to new collagen production. Subjective improvement of the treated areas increased over a six month followup, however, widespread use of this product will depend on more long term results.

Injectable Synthetic Material

Lemperle et al. described results with ARTEPLAST™, a product developed by Rofil Medical International BV. ARTEPLAST™ is an injectable material composed of microspheres of polymethylmethylacrylate (PMMA) suspended in a gelatin solution. Following implantation, the gelatin is resorbed and replaced by native collagen.

ARTECOLL™ is a product, currently available in Europe and Canada, that the FDA is considering for use in the United States. ARTECOLL™ consists of smooth 30 to 40 micron PMMA spheres, suspended in bovine collagen from a closed pharmaceutical herd at a concentration of 25% PMMA, 75% collagen, by weight with 0.3% lidocaine. Because ARTECOLL™ contains bovine collagen, skin testing for allergy to bovine collagen is recommended. Although the PMMA beads averaged 30 to 40 microns in size, and are thus theoretically subject to phagocytosis by macrophages, no phagocytosis of PMMA spheres was detected.

Silicone injection into facial soft tissues became popular during the 1960's and 1970's, due to Dow Corning's introduction of medical grade silicone (MDX 4-4011). Silicone appears to be tolerated when in small amounts in the face and can be injected interdermally or subcutaneously. Microdroplets of silicone are dispersed within dermal tissues and are individually surrounded by foreign body reactions. Fibrosis around these droplets localizes the material, but a low grade inflammatory process remains.

A distinct drawback of injectable liquid silicone (350 cS viscosity) is that particles may migrate if the silicone is used in large quantities. Silicone particles have been found in the liver, brain, lungs, and kidneys. Injection of small quantities of medical silicone, less than two milliliters, is successful and safe for the treatment of hemifacial atrophy and other tissue deficiencies of the face. However, liquid silicone used in large doses can provoke serious general complications due to the migration of the particles.

Another injectable synthetic material is TEFLON™, produced by Dupont. TEFLON™ is inappropriate for usage in the face because migration of small particles of TEFLON™ paste and solid TEFLON have been reported.

Bioplastique™

Uroplasty BV designed BIOPLASTIQUE™, a biphasic material, consisting of solid silicone particles, ranging from 100 to 400 microns in size, suspended in a polyvinylpyrridolone $((C_6H_9NO)_n)$ carrier (PVP). Bioplastique elicits a low-grade inflammatory response upon injection. In a rabbit model, the hydrogel carrier is reabsorbed by the body within 96 hours and renally eliminated in an intact form.

The hydrogel carrier is replaced by fibrin and inflammatory cells. Fibroblasts are recruited into the area by 14 days and begin to replace the fibrin bed with a collagen matrix. The collagen encapsulates and localizes the silicone, and animal studies have not shown any evidence of foreign body migration. Deposition of collagen progresses, replacing the organic component of the material in a ratio slightly greater than 1:1. Connective tissue cells develop and replace about 30% of the matrix with host collagen fibrils. At day 382 after injection, fibrosis was complete, and each individual BIOPLASTIQUE™ microimplant particle appeared to be encased in its own fibrous capsule.

Animal studies showed that BIOPLASTIQUE™ is very stable. Neither histologic examination of the regional lymph nodes at the base of the rabbit ears or cross-sections of the ear below the injected area showed microimplant particles in any of the rabbits under study.

The gel phase of the biphasic BIOPLASTIQUE™ is PVP, a member of the plasdone family. The gel is scavenged by the reticuloendothelial system and excreted unchanged by the kidneys within a matter of days. The PVP used in BIOPLASTIQUE has a molecular weight between 15,000 and 30,000 Da and has an appearance and consistency similar to that of honey. The plasdones have been used as vehicles and extenders for a variety of medications without negative effects for nearly fifty years.

BIOPLASTIQUE™ is generally implanted through a blunt, 20 gauge cannula and remains where it is placed. Complications may arise when too much material is placed in the skin or if the material is placed too close to the skin surface. BIOPLASTIQUE™ should only be used deep under the skin and never in the skin. BIOPLASTIQUE™ currently does not have FDA approval, but the manufacturer is evaluating an identical product, Macroplastique, for urethral incontinence under an FDA investigational drug exemption.

BIOPLASTIQUE™ has the distinct disadvantage of using silicone as the solid substrate. The solid phase of BIOPLASTIQUE™ is fully polymerized and vulcanized methyl methylpolysiloxane $[(CH_2)_2—SiO]$. Questions exist about the long-term safety of silicone materials.

Though many options exist for augmentation materials and methods, none of them are provide adequate augmentation. Therefore, what is needed are methods and compositions comprising safe, predictable, and solid injectable materials for tissue augmentation.

SUMMARY OF THE INVENTION

The present invention generally relates to methods and compositions comprising inert injectable materials for soft tissue volume replacement, and particularly to compositions having multiple components, and more particularly to compositions comprising a biphasic injectable material, comprising a solid polymer particle phase and a gel phase. A preferred embodiment of the present invention comprises Gore-Tex (e-PTFE, an expanded, fibrillated form of polytetrafluoroethelene (PTFE)) as the solid polymer particle phase. The hydrogel carrier phase of a preferred embodiment comprises polyvinylpyrrolidone (PVP), a member of a family of polymers that have been used pharmaceutically for nearly fifty years.

Other aspects of the invention include solid polymer particles made from materials including but not limited to, PDS II (polydioxanone, a monofilament), NUROLON (a long chain aliphatic polymer Nylon 6 or Nylon 6,6) ETHILON (a long chain aliphatic polymer Nylon 6 and Nylon 6,6), PROLENE (Polypropylene, isotactic crystalline stereoisomer of polypropylene, a synthetic linear polyolefin.), VICRYL (copolymer made from 90% glycolide and 10% L-lactide), silk, MONACRYL (poly ε-caprolactone.), polylactide, polyglycolide, poly lactide-co-glycolide, MEDPOR (biocompatible (micronized) polyethylene), BIOGLASS (bioactive glass particulate), NOVABONE, NOVABONE-CM, and BIOPOL (polyhydroxyvalerate). These inert polymers have all been approved for medical use and are used in suture and implant materials. These polymers provide a solid phase for at least more than three days. Such polymers may remain solid within the body for a long time or may be resorbed by the body in a few weeks. The use of the term "solid polymer" comprises both long-lasting polymers and polymers that are resorbed by the body.

One embodiment of the present invention provides compositions of multiple materials for use in tissue augmentation. One embodiment of the present invention provides compositions of a biphasic injectable material for use in soft tissue augmentation, such as subcutaneous placement. Another embodiment of the present invention also provides methods of use of compositions, which comprise single phase compositions such as PVP which are useful for effacing fine rhytids, such as crows feet, depressed acne scars, perioral rhytids, stretch marks and furrows. Such compositions are particularly useful in methods of intradermal augmentation. The compositions of the present invention can be used for tissue augmentation at any site in the body where tissue bulking or augmentation is needed, whether for functional or aesthetic purposes. A particularly preferred method comprises using the compositions of the present invention for urological conditions.

Accordingly, it is an object of the present invention to provide methods for tissue augmentation and compositions that are permanent or that may be resorbed by the body, resistant to infection, resistant to extrusion and non-antigenic.

Another object of the present invention is to provide compositions comprising particles of a size that are large enough to prevent ingestion by macrophages and to prevent migration to distant sites after implantation.

It is another object of the present invention to provide methods for tissue augmentation and compositions that are moldable following implantation, but stable after remolding, and that mimic the consistency of the tissue that it replaces.

Still another object of the present invention is to provide methods for tissue augmentation and compositions that are useful in soft tissue augmentation that is mechanically stable with respect to the surrounding tissues.

Yet another object of this invention is to provide a method for treating stress incontinence through functional augmentation.

These and other objects, features and advantages of the present invention will become apparent after a review of the following detailed description and claims.

DETAILED DESCRIPTION OF THE INVENTION

The present invention may be understood more readily by reference to the following detailed description included herein. Although the present invention has been described with reference to specific details of certain embodiments thereof, it is not intended that such details should be regarded as limitations upon the scope of the invention. The entire text of the references mentioned herein are hereby incorporated in their entireties by reference.

The present invention is directed to methods of tissue augmentation and novel compositions of injectable material suitable for soft tissue replacement that are permanent or semi-permanent, biocompatible, moldable, mechanically stable, and have the consistency of the tissues that are replaced.

Though encapsulation of smooth surfaces occurs readily, in general, tissue ingrowth occurs when implant surfaces are textured or patterned, and the ingrowth prevents host-prosthesis interface micro-motion, resulting in a more intimate mechanical bond between the mammalian host and the inert implant. In addition, studies by Taylor and Gibbons, Whalen, Beisang, and Ersek, and others demonstrate that the use of textured surfaces results in a thinner, less reactive encapsulation than smooth-surfaced implants in the same animal at the same time.

Implant infection can occur either by direct inoculation (e.g., placement of an implant through a contaminated area) or hematogenously. In addition, implant pores provide a potential space for infection to develop if these spaces are not occupied by host tissues. Merritt et al. showed that porous implants are more susceptible to early infection, but less susceptible to late infection, when compared to solid implants. Similarly, Scalfani et al. showed that the presence of soft tissue ingrowth into porous implants has a protective effect against experimentally-induced infections.

Studies by Zimmerii et al. and others showed that the presence of an implant diminishes local cell-mediated immunity. Decreases in hemolytic complement levels, complement-mediated opsonization, and neutrophil bacteriocidal activity have been shown to occur in the presence of a foreign body. Tissue ingrowth and macrophage migration into porous implants is limited when pore sizes are less than fifty microns, however, bacteria can invade the implants if the pores are greater than one micron. Therefore, materials with pores between one and fifty microns are susceptible to bacterial invasion, with little chance of an effective host immune response. Host vascular ingrowth provides granulation tissue that fills the dead space of implant interstices and creates an avenue for inflammatory cells to respond to a developing infection.

The present invention comprises methods of use of compositions comprising multiple materials, such as solid particles and a carrier. A most preferred solid particle comprises micronized particles of e-PTFE ("Gore-Tex"). Other materials that are suitable for use in the present invention include, but are not limited to, PDS II (polydioxanone, a monofilament), NUROLON (a long chain aliphatic polymer Nylon 6 or Nylon 6,6) ETHILON (a long chain aliphatic polymer Nylon 6 and Nylon 6,6), PROLENE (Polypropylene, isotactic crystalline stereoisomer of polypropylene, a synthetic linear polyolefin.), VICRYL (copolymer made from 90% glycolide and 10% L-lactide), silk, MONACRYL (poly $\epsilon$-caprolactone.), polylactide, polyglycolide, poly lactide-co-glycolide, MEDPOR (biocompatible (micronized) polyethylene), BIOGLASS (bioactive glass particulate), NOVABONE, NOVABONE-CM, and BIOPOL (polyhydroxyvalerate). These inert polymers have all been approved for medical use and are routinely used in suture and implant materials. Carriers that are suitable for use in the present invention include, but are not limited to, PVP, silicone oil, saline, gelatin, collagen, autologous fat, hyaluronic acid, autologous plasma and other physiological carriers.

Preferred embodiments of the present invention comprise compositions comprising solid particles of Gore-Tex of an injectable size. This material is nontoxic, physically stable, and chemically biocompatible. Gore-Tex is manufactured as an expanded, fibrillated form of polytetrafluoroethelene (PTFE). Compositions comprising Gore-Tex provide a much more stable implant than other materials used in relatively large implants. Such textured microparticles in the compositions of the present invention lead to a more lasting implant result.

Other embodiments of the invention comprise combinations of materials for injecting for tissue augmentation. For example, a combined composition may comprise Gore-Tex, fat, and collagen. The carrier material may be PVP, water, saline, or other solutions that are capable of being injected and act as a carrier for the solid particles. Any of the known materials for tissue augmentation may be used in combinations of the present invention, though most preferable combinations comprise these materials and Gore-Tex.

Sheets of Gore-Tex material have been used in tissue augmentation. Pores between the PTFE fibrils in Gore-Tex average about twenty-two microns in size and allow limited soft tissue ingrowth. Gore-Tex evokes a mild chronic inflammatory response and is rapidly surrounded by a thin fibrous capsule. At present, sheets of Gore-Tex have been used in subcutaneous volume augmentation on the chin, malar area, nasal dorsum, nasolabial folds, and lips.

e-PTFE is a suitable implant for soft tissue augmentation of the face because of its soft, natural feel and high biocompatibility. Although larger e-PTFE implants in mobile facial areas make removal possible and provide easy sterilization, they are also unstable due to the limited implant surface for tissue ingrowth which results in inflammation and extrusion.

Advantages of the present invention comprising Gore-Tex particles are that limited fibrous tissue ingrowth into the surface of the material provides early stabilization, while allowing for removal if necessary. Gore-Tex is inert and does not change shape or reabsorb with time. Additionally, Gore-Tex is not carcinogenic, rarely allergenic, and causes only minimal tissue reaction. After implantation, fibrous encapsulation inhibits breakdown of the particles. The size of the particles prevents the material from being phagocytosed, and thus, it does not serve as an antigen. In addition, the absence of eosinophilia, a hallmark of delayed hypersensitivity, makes it unlikely that Gore-Tex is antigenic or haptenic. Histology demonstrated that hypersensitivity granuloma formation does not occur and that only macrophages and mature collagen are present over time.

Though not wishing to be bound by any particular theory, it is theorized that because particles greater than sixty microns in size have never been found within a cell or lymph node, the critical particle size to prevent migration is at least greater than sixty microns and preferably, eighty microns. A more preferred embodiment of the present invention comprises compositions comprising particles greater than one hundred microns in size with a textured surface. Such compositions are interspersed in a host-generated fibrotic tissue matrix within a few weeks. Compositions of the present invention comprise particles having a size range of approximately 60 microns to approximately one millimeter are useful in methods for soft tissue augmentation. For other methods, differently sized particles are contemplated by the present invention.

Applicants have discovered novel compositions of injectable material suitable for tissue replacement that are biocompatible, moldable, mechanically stable, and have a consistency similar to the tissue that it replaces. Such compositions may be used in methods of tissue augmentation known to those in the surgical arts. Preferably, the biphasic compositions are injected into tissue sites, and most preferably, are used in subcutaneous injection methods. Additional preferable methods include methods of injection of the compositions of the present invention in tissue sites such as those in the urethra or other urological sites. Other preferable sites include tissue sites such as the vocal cords.

Another embodiment of the present invention includes polyvinylpyrrolidone (PVP) as a tissue augmentation material. PVP is a water-soluble polyamide that possesses unusual complexing and colloidal properties and is physiologically inert. It does not act as a skin or eye irritant or as a skin-sensitizer. PVP is well tolerated by intraperitoneal, intramuscular, and intravenous routes, as well as parenteral uses such as usage for plasma volume expansion. No cancer effect for PVP has been demonstrated by any route.

PVP is a biocompatible gel vehicle that is freely transported through the body and is excreted unchanged by the kidneys. This gel has the trade name Au24k and consists of macromolecules from the plasdone family, having the empirical formula $(CHCH_2)_2N(CH_2)_3$—CO. Polymers of this family have been used as binders, extenders, and vehicles for a variety of medications for nearly fifty years. In fact, over 4,000 papers have been published on the use of PVP in pharmacy and medicine since 1940.

PVP is available commercially in many molecular weight ranges and is polymerized to have an average molecular weight in a particular solution. For example, PVP is available in solutions of an average molecular weight of 10,000 daltons, 40,000 daltons and 360,000 daltons. PVP is also defined by its viscosity measurement, or K value. K values range from approximately less than 12 to 100. A preferred PVP composition of the present invention has a range of K values of less than 12 to 50, more preferably less than 12 to 20, and most preferable is a composition of K17. PVP is commercially available from GAF Chemical Corp., Wayne, N.J., USA, and from BASF Aktiengesellschaft, Germany.

In use, the gel polymer may be diluted with deionized water to produce the desired osmotic gradient, is sterilized, and placed in cartridges for injection.

An inflammatory reaction due to the reabsorption of the PVP occurs a few days after implantation, and the PVP undergoes a prompt replacement by host fibrin or protocollagen within 96 hours. As this fibrin substitution is completed, fibroblasts appear within the matrix and begin fabricating host collagen by the sixth day; by the sixth week, this fibrosis is complete. The result is stable and final after approximately three months.

A preferred composition of the present invention comprises solid substrate particles of Gore-Tex (e-PTFE) ranging in size from one hundred to two hundred microns mixed with PVP hydrogel. The composition has all of the desirable characteristics of an injectable soft tissue implant. The small Gore-Tex particles, having a textured surface, form an inert biocompatible polymer that can be mixed, at a range 5:95 to 95:5, more preferably 20:80, most preferably 40 to 60, by weight, with a biocompatible solution of water and organic polymer gel. Utilizing the hydrogel carrier PVP not only promotes ingrowth, but also provides a barrier to bacterial invasion of the textured e-PTFE surface.

Preferred methods include injection of such biphasic compositions, more preferably, the compositions are injected subcutaneously. Other injection sites such as intramuscular and intradermal are included in the methods of the present invention. Preferred methods include tissue bulking methods, particularly for urological conditions. For example, the compositions of the present invention are injected into the walls of the urethra to aid in the treatment of incontinence. Other methods of tissue bulking are also contemplated by the present invention, such as for vocal cord augmentation or repair.

Another embodiment of the present invention comprises compositions comprising carriers such as PVP or known physiological carriers in combination with materials, including but limited to, collagen, bovine or human, other particles made from materials such as PDS II (polydioxanone, a monofilament), NUROLON (a long chain aliphatic polymer Nylon 6 or Nylon 6,6) ETHILON (a long chain aliphatic polymer Nylon 6 and Nylon 6,6), PROLENE (Polypropylene, isotactic crystalline stereoisomer of polypropylene, a synthetic linear polyolefin.), VICRYL (copolymer made from 90% glycolide and 10% L-lactide), silk, MONACRYL (poly ε-caprolactone.), polylactide, polyglycolide, poly lactide-co-glycolide, MEDPOR (biocompatible (micronized) polyethylene), BIOGLASS (bioactive glass particulate), NOVABONE, NOVABONE-CM, and BIOPOL (polyhydroxyvalerate) or oils. These materials are injected, preferably subcutaneously.

The present invention further utilizes methods and compositions for tissue augmentation that comprise injection of PVP for tissue augmentation, preferably intradermal injection, particularly for fine rhytids, such as crows feet, depressed acne scars and perioral rhytids.

PVP undergoes a prompt replacement by host fibrin or protocollagen within 96 hours. As this fibrin substitution is completed, fibroblasts appear within the matrix and begin fabricating host collagen by the sixth day; by the sixth week, this fibrosis is complete. The result is stable and final after about three months.

Preferred methods of the present invention comprise use of PVP as an intradermal injection material to generate deposition of host collagen to efface fine rhytids such as crows feet, depressed acne scars and perioral rhytids.

Modifications can be made to the invention herein disclosed with respect to the illustrated embodiments, without departing from the spirit of the instant invention. And while the invention has been described below with respect to the examples, it will be understood that the invention is adapted to numerous rearrangements, modifications, and alterations, all such arrangements, modifications, and alterations are intended to be within the scope of the appended claims.

EXAMPLES

Example 1

The preparation of the intradermal sites to be injected are cleansed initially with a germicidal soap such as Hibiclens®. The patient is then marked in the upright position with a fine surgical marking pen and those areas marked are lightly swabbed with alcohol prior to injection with the patient in the supine position. Diffuse overhead light is the best illumination when injecting the face. A bright light directed onto the face does not allow shadows to be cast which further identify the lines, depressions, scars, etc. that are outlined in ink. The serial puncture technique is utilized: the thumb is placed one centimeter behind the index finger as both digits of the left hand (if one is right-handed) straddle and raise the affected area. The needle is repeatedly inserted (at an oblique angle) into the skin between the thumb and finger at intervals of several millimeters along the course of the wrinkle, depression or area to be augmented.

This Example is directed to intradermal use, primarily. The injectable techniques illustrated herein can also be adapted to subcutaneous, intramuscular, periurethral or other deeper injection sites with a biphasic augmentation material for functional or cosmetic applications.

Example 2

Common cosmetic applications include intramuscular lip augmentation and subcutaneous augmentation of the nasolabial creases. Special blunt 20-gauge cannulas measuring about 4 inches in length are attached to a leveraged "gun" that receives syringe cartridges. This gun allows very precise injection of the material in small, evenly spaced quantities of the biphasic augmentation material. First the area to be treated is outlined with a pen, and the estimated volume is recorded. This area is then injected with lidocaine with epinephrine to provide anesthesia and to minimize bleeding. Through a remote puncture site, the blunt cannula is then introduced to the subcutaneous tissue. In a scarred area such as a cleft lip, it may be necessary to pretunnel with a pencil tip trocar to create a series of sponge-like channels to accept the material without bunching or beading. In the uninjured lip for augmentation, no such pretunneling is required, and the blunt cannula is simply passed to-and-fro along the length of the lip approximately in the middle of the muscle mass. One must be very careful to inject very slowly while moving the cannula very rapidly. One-tenth of a cubic centimeter of this biphasic material makes a line 30 cm in length so that if a stroke is 5 cm in length, six strokes would be required to evenly place such a fine bead of material in multiple parallel paths to avoid bunching. Thus, the blunt cannula would be passed to-and-fro the substance of the lip muscle and can deliver this fine bead of material. During six such passes a single click of the ratcheted, levered gun would deliver that 0.1 cc. As a result of experience, 0.2 cc or less, is injected in the upper lip or the lower lip at one time. In this way, an even distribution of the material with minimal trauma to the surrounding surface can be achieved.

Example 3

Subcutaneous cosmetic augmentation of the nasolabial creases and reconstructive augmentation of iatrogenic or traumatic lipodystrophy (dents due to subcutaneous fat loss) are performed in a similar fashion. After careful demarcation of the proposed augmentation site, the entire area is injected with Xylocaine 1% with epinephrine 1:100,000, providing the local block needed as well as hemostasis. A remote puncture is then performed with a 18-gauge sharp needle on each side of the area for augmentation, peripheral to the outlined area, so that 1 to 2 cm of "no-man's land" isolates the puncture sites from the area of planned implantation. Pretunneling is done in various planes. The microparticles are then implanted from the same remote puncture site by means of the injection gun. Injection is done only on withdrawal, mimicking the path and technique of the pocar and injecting only to the midline. The cannula is kept in constant motion, and trigger pressure is gently maintained on withdrawal such that a 0.1-cc volume injection is 30 cm in length. These methods allow precise and even placement of the solid phase microparticles at the intended plane and prevent deposition near the puncture site, which could impede healing of the dermis and result in palpable elevations. Such techniques also provide a maximum host-prosthesis interface and a minimum of beading or coalescing of these particles. After injection, the pressure is released in the gun and the cannula quickly withdrawn. Digital pressure is applied to the midline while the puncture site and "no man's land" are rinsed with local anesthesia to further prevent extrusion.

Example 4

Functional augmentation with the biphasic injectable may be utilized in treatment of stress incontinence. In the case of females, the patient is placed in the lithotomy position. The vulva and vagina are cleansed and the patient is draped as for a cystoscopic procedure. The urethra is calibrated with a bougie for evidence of strictures. Cystoscopy and urethroscopy are performed. A 20 gauge needle, approximately 4 inches long, is attached to a Lewy syringe that has been loaded with biphasic augmentation material, inserted at the urethral meatus and advanced periurethrally toward the bladder neck. At this point several cubic centimeters of the paste are injected. The injection is continued as the needle is withdrawn. The procedure is performed at approximately 3, 6 and 9 o'clock positions around the urethra. At the 6 o'clock position the needle can be guided along the narrow septum between the urethra and vagina with an examining finger in the vagina. Approximately 10 to 15 ml. of paste are injected. The urethra is inspected with a panendoscope during the injections to be certain that the needle has not perforated the bladder or urethra. As the injection progresses resistance develops to the movement of the panendoscope in the urethra. In male patients, the external genitalia and the perineum are carefully cleansed and draped. As with the female patients, the urethra is calibrated to be certain that strictures are not present. Urethrograms are obtained when necessary. The bladder and urethra are inspected with careful attention to the prostatic and membranous urethra. The panendoscope is left in the urethra as a 17 gauge needle is inserted into the perineum and advanced toward the apex of the prostate. By gentle to and fro motion one can observe the tip of the needle advancing toward the region of the external sphincter. Care is taken to avoid penetration of the urethral lumen, which would provide an escape for the biphasic augmentation material. When the needle has been advanced into its proper position the Lewy syringe is attached and the injections are started. The needle is advanced, withdrawn or moved to a new position when appropriate to try to produce complete closure or narrowing of the membranous urethra. The injection can be monitored through the panendoscope and the blebs produced by the injections are visualized clearly. Generally, 15 cc of the paste are injected. An alternate method is to enter the lumen of the urethra several centimeters away from the area to be injected. The needle is advance through the lumen and the urethral wall is penetrated a few millimeters from the area to be injected. The needle tip is advanced within the urethral wall and the paste is injected.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

The following references are hereby incorporated by reference in their entirety.

1. Allen O. Response to Subdermal Implantation of Textured Microimplants in Humans. AestheticPlasticSurgery 1992; 16:227-230
2. Beisang A A, Ersek R A. Mammalian Response to Subdermal Implantation of Textured Microimplants. Aesthetic Plastic Surgery 1992;16:83-90
3. Boros D L. Granulomatous inflammations. Prog Allergy 1978;24:212
4. Boss WK, Marko O. Isolagen. In: Klein A W, ed., Tissue Augmentation in Clinical Practice; Procedures and Techniques, New York: Marcel Dekker; 1998:335-347
5. Choe K S, Stucki-McCormick S U. Chin Augmentation. Facial Plastic Surgery 2000; 16:45-54
6. Costantino P D, Friedman C D, Lane A. Synthetic biomaterials in facial plastic and reconstructive surgery. Fac Plast Surg 1993;9:1-15
7. Davichon R L (Ed.) Handbook of Water Soluble Gums and Resins. New York: McGraw-Hill, 1980. Chap. 21.
8. Davidson R L (Ed.). Handbook of Water Soluble Gums and Resins 1980;Chap.21
9. Dewan P A, Byard R W. Histological response to injected polytef and Bioplastique in a rat model. DBr J Urol 1994;73:370-376
10. Dewan P A, Owen A J, Byard R W. Long-term histological response to subcutaneously injected Polytef and Bioplastique in a rat model. Br J of Urology 1995;76: 161-164
11. Environ Corporation: Summary of published literature on the health effects of injectable silicone fluids. Washington D.C., August 1987:1-40
12. Ersek R A. Bioplastique™: Specific Technical Advice on Its Use and Possible Complications. Aesthetic Plastic Surgery 1992;16:67-68
13. Ersek R A. Prostheses for breast augmentation: Progress in materials and the design of these implants continues. Travis County Med Soc J 8-10, May 1989
14. Ersek R A, Beisang A A. Bioplastique™: A New Textured Copolymer Microparticle Promises Permanence in Soft-Tissue Augmentation. Plastic and Reconstructive Surgery 1991;87:693-702
15. Ersek R A, Beisang A A. Bioplastique™: A New Biphasic Polymer for Minimally Invasive Injection Implantation. AesIthetic Plastic Surgery 1992;16:59-65
16. Ersek R A, Gregory S R, Salisbury A V. Bioplastique at 6 years: Clinical Outcome Studies. Plastic and Reconstructive Surgery 1997;100:1570
17. Ersek R A, Kjellstrans C, Lillehei R C. A new arteriovenous shunt design. ASAIO, XV: 267, 1969 (U.S. Pat. No. 3,638,649, Implantable Prosthetic Device, 1972)
18. Ersek R A, Stovall R B, Vasquez-Salisbury A. Chin Augmentation Using Minimally Invasive Technique and Bioplastique. Plastic and Reconstructive Surgery 1995; 95:986
19. Klock J C, Stossel T P. Detection, pathogenesis and prevention of damage to human granulocytes caused by interaction with nylon wool fiber: Implications for filtration leukapheresis. J Clin Invest 1977;60: 1183-1190
20. Lemperle G, Hazan-Gauthier N, Lemperle M. PMMA Microspheres (Artecoll) for Skin and Soft-Tissue Augmentation. Part II: Clinical Investigations. Plastic and Reconstructive Surgery 1995;96:627-634
21. Levine B, Berman W E. The current status of expanded polytetrafluoroethylene (Gore-Tex) in facial plastic surgery. ENT 1995;74(10):681-684
22. Mass C S, Eriksson T, McCalmont T, Mabry D, Cooke D, Schindler R. Evaluation of Expanded Polytetrafluoroethylene as a Soft-Tissue Filling Substance: An Analysis of Design-Related Implant Behavior Using the Porcine Skin Model. Plastic and Reconstructive Surgery 1998; 101: 1307-1314
23. Mass C S, Gnepp D R, Bumpous J. Expanded polytetrafluoroethylene (Gore-Tex soft-tissue patch) in facial augmentation. Arch Otolaryngol Head Neck Surg 1993; 119:1008
24. Merritt K, Shafer J W, Brown S A. Implant site infection rates with porous and dense materials. J Biomed Mater Res 1979; 13:101-108
25. Mole B. The use of Gore-Tex implants in aesthetic surgery of the face. Plast Reconstr Surg 1992;90(2):200-206

26. Morehead J M, Holt G R. Soft-tissue response to synthetic biomaterials. Otolaryngology Clin NA 1994;27: 195-201
27. Nijhuis P H, van den Bogaard T E, Daemen M J, Baeten C G. Perianal Injection of Polydimethylsiloxane (Bioplastique™ Implants) Paste in the Treatment of Soiling: Pilot Study in Rats to Determine Migratory Tendency and Locoregional Reaction. Dis Colon Rectum 1998;41:625
28. Paicquadio D, Jarcho M, Goltz R. Evaluation of hylan b gel as a soft-tissue augmentation implant material material. J Am Acad Dermatol 1997;36:544-549
29. Politano, Victor A., Periurethral Polytetrafluorethylene Injection for Urinary Incontinence. The Journal of Urology 1982; 439-442.
30. Robinson B V, Sullivan F M, Borzelleca J F, Schwartz S L. PVP: A Critical Review of the Kinetics and Toxicology of Polyvinylpyrrolidone (Povidone). Chelsea, Mich.: Lewis Publishers, Inc., 1990
31. Romo T, Sclafani A P, Sabini P. Use of porous high-density polyethylene in revision rhinoplasty and in the platyrrhine nose. Aesth Plast Surg 1998;22:211-221
32. Schoenrock L D, Reppucci A D. Correction of subcutaneous facial defects using Gore-Tex. Facial Plast Surg Clin N AM 1994;2:373-388
33. Sclafani AP, Romo T. Biology and Chemistry of Facial Implants. Facial Plastic Surgery 2000; 16:3-6
34. Sclafani A P, Romo T. Injectable Fillers for Facial Soft Tissue Enhancement. Facial Plastic Surgery 2000;16:29-34
35. Sclafani A P, Thomas J R, Cox A J, Cooper M H. Clinical and histological response of subcutaneous expanded polytetrafluroethylene (Gore-tex) and porous high density polyethylene (Medpor) implants to acute and early infection. Arch Otolaryngol Head Neck Surg 1997; 123:328-336
36. Silver F H, Maas C S. Biology of synthetic facial implant materials. Fac Plast Surg Clin of North Am 1994;2:241-253
37. Simons G, Mazaleyrat P, Masurel T. Utilization of Injectable Microimplants in Aesthetic Facial Surgery. Aesthetic Plastic Surgery 1992;16:77-82
38. Smahel J. Tissue reactions to breast prostheses coated with polyurethane. Plast ReconstrSurg 1978;61:80
39. Staffel G, Shochley W. Nasal Implants. Otolaryngol Clin NA 1995;28:295-308
40. Stucker F J. Use of implantation in facial deformities. Laryngoscope 1977;87: 15231528
41. Tang L, Eaton J W. Inflammatory response to biomaterials. Am J Clin Pathol 1995;103:466-471
42. Taylor S R, Gibbons D F. Effect of surface texture on the soft tissue response to polymer implants. Journal of Biomedical Materials Research 1983; 17:205-227
43. Tolleth H. Long-term effcacy of collagen. Aesth Plast Surg 1985;9: 155-158
44. Watson D, Keller G S, Lacombe V, Fodor P B, Rawnsley J, Lask G P. Autologous fibroblasts for treatment of facial rhytids and dermal depressions. Arch Facial Plast Surg 1999; 1:165-170
45. Webster R C, Fuleihan N S, Hamdan U S, Smith R C: Use of injectable silicone for augmentation of facial contours. In: English GM (ed): Otolaryngology. Philadelphia: Lippincott Company, 1988, chap 53, p 2.
46. Whalen R E Connective Tissue Response to Movement at the Prosthesis/Tissue Interface. In M. Zycher (Ed.), Biocompatible Polymers, Metals and Composites. Lancaster, Pa.: Technomic, 1983.
47. Zimmerli W, Waldvogel F A, Vaudaux P, Nydegger U E. Pathogenesis of foreign body infection: Description and characteristics of an animal model. J Infect Dis 1982;146: 487-497

What is claimed is:

1. A biphasic injectable composition for tissue volume, comprising:
    a solid polymer phase; and
    a carrier substrate phase,
    wherein the solid polymer phase is made from micronized expanded polytetrafluoroethelene ("e-PTFE") particles, polydioxanone, Nylon 6, Nylon 6,6, polypropylene, copolymer made from 90% glycolide and 10% L-lactide, silk, poly E-caprolactone, polylactide, polyglycolide, poly lactide-co-glycolide, polyhydroxyvalerate, biocompatible micronized polyethylene, bioactive glass particulate, synthetic bone graft particulate, or polyhydroxyvalerate.

2. The composition of claim 1, wherein the solid polymer phase is made from at least two of micronized expanded polytetrafluoroethelene ("e-PTFE") particles, polydioxanone, Nylon 6, Nylon 6,6, polypropylene, copolymer made from 90% glycolide and 10% L-lactide, silk, poly E-caprolactone, polylactide, polyglycolide, poly lactide-co-glycolide, polyhydroxyvalerate, biocompatible micronized polyethylene, bioactive glass particulate, synthetic bone graft particulate, or polyhydroxyvalerate.

3. The composition of claim 1, wherein the carrier substrate phase is selected from polyvinylpyrrolidone ("PVP"), silicone oil, gelatin, collagen, fat, hyaluronic acid, water or plasma.

4. The composition of claim 1 wherein the solid polymer phase comprises micronized expanded polytetrafluoroethelene ("e-PTFE") particles.

5. The composition of claim 4, wherein the e-PTFE particles range in size from approximately 65 to 1000 micrometers.

6. The composition of claim 1, wherein the carrier substrate phase is PVP.

7. The composition of claim 6, wherein the PVP comprises a K value from approximately less than 12 to 100.

8. The composition of claim 6, wherein the PVP comprises a K value from approximately less than 12 to 50.

9. The composition of claim 6, wherein the PVP comprises a K value from approximately less than 12 to 20.

10. The composition of claim 6, wherein the PVP comprises a K value of 17.

11. The composition of claim 1, wherein the solid polymer phase comprises e-PTFE;
    and the carrier substrate phase comprises PVP.

12. The composition of claim 11 wherein the e-PTFE and the PVP are combined at a ratio of approximately 3:2 PVP to ePTFE by weight.

13. The composition of claim 1, wherein the carrier substrate phase comprises micronized polydioxanone particles ranging in size from approximately 65 to 1000 micrometers.

* * * * *